(12) United States Patent
Ankuda, Jr. et al.

(10) Patent No.: US 6,638,605 B1
(45) Date of Patent: Oct. 28, 2003

(54) INTERMITTENTLY BONDED NONWOVEN DISPOSABLE SURGICAL LAMINATES

(75) Inventors: Edward J. Ankuda, Jr., El Paso, TX (US); Eric S. Thompson, El Paso, TX (US); Joe Miller, El Paso, TX (US); Daniel L. Swanberg, El Paso, TX (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/441,310

(22) Filed: Nov. 16, 1999

(51) Int. Cl.$^7$ .................. B32B 27/14; V04H 3/12
(52) U.S. Cl. ............... 428/198; 428/200; 428/201; 428/339; 428/95; 442/381; 442/409; 156/291; 604/358; 604/380
(58) Field of Search ............ 428/198, 200, 428/201, 339, 95; 604/380, 351; 156/291; 442/381, 409

(56) References Cited

U.S. PATENT DOCUMENTS

| | | | |
|---|---|---|---|
| 3,327,708 A | 6/1967 | Sokolowski | 602/45 |
| 3,507,943 A | 4/1970 | Such et al. | 264/103 |
| 3,704,197 A * | 11/1972 | Bahlo | 428/85 |
| 3,745,301 A * | 7/1973 | Sherrill et al. | 219/212 |
| 3,953,638 A | 4/1976 | Kemp | 428/154 |
| 4,005,169 A | 1/1977 | Cumbers | 264/103 |
| 4,170,680 A | 10/1979 | Cumbers | 428/195 |
| 4,209,563 A | 6/1980 | Sisson | 442/329 |
| 4,493,868 A | 1/1985 | Meitner | 428/171 |
| 4,525,407 A | 6/1985 | Ness | 428/138 |
| 4,726,976 A | 2/1988 | Karami et al. | 428/137 |
| 4,778,460 A | 10/1988 | Braun et al. | 604/380 |
| 4,863,785 A | 9/1989 | Berman et al. | 428/218 |
| 4,961,985 A | 10/1990 | Henn et al. | 428/196 |
| 4,996,722 A | 3/1991 | Jimenez et al. | 2/51 |
| 5,143,679 A | 9/1992 | Weber et al. | 264/288.8 |
| 5,151,092 A | 9/1992 | Buell et al. | 604/385.3 |
| 5,151,314 A * | 9/1992 | Brown | 428/198 |
| 5,156,793 A | 10/1992 | Buell et al. | 264/288.8 |
| 5,167,897 A | 12/1992 | Weber et al. | 264/288.8 |
| 5,221,274 A | 6/1993 | Buell et al. | 604/385.3 |
| 5,229,191 A | 7/1993 | Austin | 428/198 |
| 5,234,423 A | 8/1993 | Alemany et al. | 604/385.3 |
| 5,236,770 A | 8/1993 | Assent et al. | 428/198 |
| 5,242,436 A | 9/1993 | Well et al. | 604/385.29 |
| 5,330,458 A | 7/1994 | Buell et al. | 604/385.24 |
| 5,458,721 A | 10/1995 | Raterman | 156/291 |
| 5,492,751 A | 2/1996 | Butt, Sr. et al. | 428/198 |
| 5,499,978 A | 3/1996 | Buell et al. | 604/385.27 |
| 5,507,736 A | 4/1996 | Clear et al. | 604/385.3 |
| 5,527,304 A | 6/1996 | Buell et al. | 604/385.25 |
| 5,560,974 A | 10/1996 | Langley | 428/198 |
| 5,591,152 A | 1/1997 | Buell et al. | 604/385.29 |
| 5,609,702 A | 3/1997 | Andersen | 156/73.1 |
| 5,635,290 A | 6/1997 | Stopper et al. | 428/198 |
| 5,653,704 A | 8/1997 | Buell et al. | 604/385.3 |
| 5,674,216 A | 10/1997 | Buell et al. | 604/385.27 |
| 5,763,041 A | 6/1998 | Leak et al. | 428/100 |
| 5,837,352 A | 11/1998 | English et al. | 428/198 |
| 5,843,057 A | 12/1998 | McCormack | 604/367 |
| 5,855,992 A | 1/1999 | Etzold | 428/198 |
| 5,883,028 A | 3/1999 | Morman et al. | 442/394 |
| 5,900,306 A | 5/1999 | Stopper | 428/198 |
| 5,901,706 A * | 5/1999 | Griesbach et al. | 128/849 |
| 5,964,742 A | 10/1999 | McCormack et al. | 604/380 |

\* cited by examiner

*Primary Examiner*—Terrel Morris
*Assistant Examiner*—John J. Guarriello
(74) *Attorney, Agent, or Firm*—Andrew G. Rozycki (57) ABSTRACT

Disposable surgical drapes and gowns exhibiting desirable softness, foldability, absorbency and breathability characteristics incorporate cluster bonded nonwoven laminates. Film layers and nonwoven web layers are secured together by spaced apart unbounded adhesive clusters. Each adhesive cluster includes a perimeterless grouping of discrete spaced apart adhesive droplets. A method and modified apparatus for making the cluster bonded laminates is also described.

22 Claims, 6 Drawing Sheets

INTERMITTENTLY BONDED NONWOVEN DISPOSABLE SURGICAL LAMINATES

BACKGROUND OF THE INVENTION

The present invention generally relates to new and improved disposable nonwoven laminates and new and improved methods for making them, as well as, to new and improved surgical drapes and gowns comprising the new and improved disposable nonwoven laminate materials. More particularly, it relates to new and improved disposable multi-ply surgical laminates including nonwoven layers in which plies of the laminate are bonded in a special flexible manner to provide materials having improved softness, hand and drapability and in which the desired material properties of layers are better retained and expressed to provide more satisfactory products.

Surgical drapes and gowns have been used to maintain a sterile field in surgery. Surgical gowns have been used in the medical community to protect health care professionals from liquids and micro-organisms during surgical and other procedures. Single use surgical gowns are typically made of nonwoven, disposable fabrics. Such gowns typically include a single body panel or multiple panels including a front panel, a pair of back panels which are connected to the sides of the front panel and extend away from the front panel, and a pair of sleeves which are provided at the juncture of the front and side panels. The front panel covers the front of the health care professional during the procedure. The back panels are secured around and overlap each other to cover the rear of the health care professional and a tying structure. Typical surgical gowns will include two outer ties and two inner ties. The inner ties are utilized to secure the inside back of the gown. The outer ties are used to ensure that the back of the gown overlaps around the rear of the health care professional.

Sterile surgical drapes are also known and widely used to create a sterile surgical field and to protect the patient. Surgical drapes come in a variety of shapes and sizes and many specialized drapes adapted for a particular type of surgery have been adopted. By way of illustration, these drapes may be provided in a rectangular sheet form for draping the operating table, covering an anesthesia procedure area, or covering the patient's legs or abdomen. More specialized drapes may include leg holes or arm holes as required for different procedures so that some portions of the patient's body remain unexposed under the drape and other portions are exposed overlying a different section of the drape. Some drapes are provided with openings or windows called fenestrations to define a bounded area around an incision site. Fenestrated drapes may have extra absorbent layers around the perimeter of the openings. Surface treatments may be used to render portions of the drapes antibacterial, antimicrobial, and/or waterproof as desired in particular surgical procedures. Simple rectangular drapes may also be used as absorbent surgical towels or wipes. Finally, the drapes may include different types of panels secured together. For example, a table drape may include a thicker absorbent table top panel and a plurality of attached side panels which have a thinner less absorbent construction to act simply as a splash guard for or to provide a barrier with respect to the underside portions of the table.

Earlier surgical drapes and gowns were constructed of woven natural fabric materials, usually cotton. These cloth articles were sterilized in the autoclave in preparation for surgery. Alternative fabrics comprising synthetic fibers were added and used. Eventually, with the advent of nonwoven fabric materials, drapes and gowns comprising nonwovens were used to provide disposable gowns and drapes adapted for one time use.

Previous drapes and gowns prepared from nonwoven materials suffer from a number of drawbacks. Typically, the nonwoven web layers are assembled with a film layer to provide a fluid impervious laminate material which is used to fashion the surgical gown. Hot melt adhesives have generally been applied over substantially the entire surface of one of the layers to bond the web and film layers together to provide the laminates. These laminates are characterized by board-like stiffness and poor drapability which makes them uncomfortable for the medical personnel who wear them. Sleeves made from these fabrics do not conform well to the wearer's wrist and frequently permit body fluids to travel along crinkled channels at the wrist under the glove cuffs and against the wearer's skin which is unacceptable. Moreover, the films used to provide an effective fluid barrier, are generally not breatheable and accordingly, gowns made from these laminates can be unbearably hot for the surgical personnel who must wear them.

Efforts to improve the softness and cloth-like quality of these nonwoven surgical laminates has lead some manufacturers to try intermittent thermal bonding of the layers through heat and pressure rollers, or ultrasonic welding techniques. The heat and pressure bonded types are undesirable because the nonwoven layers are crushed and fused in the process which detracts from their desired properties such as loft, flexibility and softness. The melt bonding points are rigid and do not bend and flex, so that the overall softness, feel and drapability properties of these materials is better but still not as good as desired. Moreover, heat bonded laminates may only be formed from appropriately heat matched thermoplastic materials, which limits the types of material layers that can be used to form the surgical laminates, placing unwanted limits on product design and ultimate product qualities.

SUMMARY OF THE INVENTION

Unexpectedly, in view of the foregoing, it has now been discovered that new and improved disposable nonwoven surgical laminates may be provided using dramatically reduced amounts of adhesive arrayed in a special bonding arrangement to provide improved disposable nonwoven surgical laminates having improved softness, hand, drapability, and comfort characteristics. In greater detail and in accordance with an embodiment of the present invention, a new and improved disposable laminate comprises a film layer, at least one nonwoven web layer and a plurality of spaced apart unbounded adhesive clusters. Each adhesive cluster comprises a plurality of discrete, spaced apart droplets of adhesive securing the film layer and the web layer together. Preferably, the adhesive clusters are spaced in a regular repeating pattern which extends the length and width of the laminate.

By unbounded is meant that the adhesive clusters do not include any applied linear boundary or perimeter of adhesive defining the cluster area. Each cluster is a perimeterless grouping of spaced apart droplets. Each cluster area is flexibly foldable in all directions with respect to the plane of the laminate which is believed to contribute to superior hand and drapability for the new and improved laminates. The low adhesive content and flexible bonding methods permit the overall softness and other desired web properties, such as absorbency, to be maintained in the laminating process and to be retained and more fully expressed in the finished laminates and products.

The film layers are preferably thermoplastic materials capable of withstanding gamma sterilization. Preferably, the thermoplastic film layers form a satisfactory fluid impervious layer capable of preventing fluid and pathogen transfer between surgical personnel and patient through the laminate. The films may be breatheable or non-breatheable. Illustrative thermoplastic films which may be used to provide the film layer include polyolefins, polyolefinic copolymers, polyesters and copolyesters to name but a few. The thermoplastic films may be made from substantially any film forming thermoplastic material suitable for close to the skin use which may withstand commercial sterilization procedures.

In a preferred embodiment, the thermoplastic film layers comprise breatheable impervious thermoplastic films selected from monolithic thermoplastic films or microporous thermoplastic films. Especially preferred films are monolithic thermoplastic copolyester elastomer films. Polypropylene based films are less preferred due to their instability under gamma sterilization processing. The film layers may generally have a basis weight of from about 0.25 to about 5.0 ounces/square yard and have a film thickness of from about 0.25 mil to about 3 mil.

The nonwoven web layers are preferably but not necessarily thermoplastic materials which can also withstand gamma sterilization processing. The nonwoven webs may be wet laid, dry laid, spunlaced, adhesive bonded, thermal bonded or spunbonded-melt blown-spunbonded (SMS) nonwoven web types. The webs may be made of thermoplastic fibers, regenerated fibers, natural fibers, and so-called bicomponent or sheath-core fibers, and may comprise mixtures of any two or more of the foregoing fiber types. The nonwoven webs may have a basis weight of from about 0.25 oz./sq. yd., to about 4.0 oz./sq. yd.

In an embodiment, the adhesives used in the laminates also comprise thermoplastic adhesives, thermosetting adhesives and/or crosslinked adhesives which can withstand gamma sterilization. Illustrative thermoplastic adhesives include olefinic polymer and copolymer adhesives, such as ethylene vinyl acetate, styrene, maleic anhydride modified polyethylene or polypropylene; polyamide adhesives, polyester and polyurethane adhesives. Illustrative thermosetting adhesives may include (meth)acrylic adhesives or styrenic adhesives to name but a few. Other adhesives conventionally employed in the field of nonwovens may also be used.

In an embodiment, new and improved two-ply laminates are provided including the film layer and a single web layer cluster bonded together. In an alternate embodiment, new and improved three-ply laminates are provided comprising a thermoplastic film layer having first and second opposed major surfaces, a first thermoplastic nonwoven web layer disposed adjacent the first major surface, a second thermoplastic nonwoven web layer disposed adjacent the second major surface, and a plurality of spaced apart unbounded adhesive clusters of spaced apart adhesive droplets securing the first web layer to the first major surface and securing the second web layer to the second major surface. In the new and improved three-ply or triplex laminates the first and second webs may be the same or different. Preferably, the film layer is a breatheable impervious thermoplastic film and the first and second nonwoven web layers comprise different web materials.

In accordance with another aspect of the invention, the present invention provides, in an embodiment, a new and improved method for making a disposable laminate. The method comprises the steps of providing a nonwoven web having a major surface and having an associated length dimension and a generally perpendicular width dimension. A plurality of discrete spaced apart droplets are deposited onto the web surface in such manner that pluralities of spaced apart droplets are arranged on the web surface in perimeterless clusters. Moreover, a plurality of these clusters are deposited on the web surface in a spaced apart manner extending generally over the length and width of the web surface. The web surface and adhesive droplets are contacted with a surface of a film layer to bond the film layer and the web layer securely but flexibly together to form the disposable laminate. In a preferred embodiment, the unbounded clusters of adhesive droplets are deposited in a regularly repeating pattern or array of adhesive clusters.

In an embodiment, droplets of adhesive are deposited in a specially arranged manner onto the web surface by providing an etched gravure roller having discrete spaced apart droplets of adhesive disposed in regular depressions defined in a circumferential surface thereof. An elastomer covered pressure roller having a circumferential bearing surface is also provided. The bearing surface of the pressure roller has a plurality of relatively raised island-like contact surfaces separated by a plurality of grooves. The pressure roller is positioned adjacent the gravure roller to form a nip therebetween so that the raised contact surfaces of the pressure roller make pressing contact with portions of the circumferential surface of the gravure roller. The grooved portions in the bearing surface of the pressure roller do not make contact with the circumferential surface of the gravure roller.

The gravure roller and pressure roller are rotated and the nonwoven web is passed into the nip between them. A portion of the spaced apart droplets of adhesive are transferred from the depressions in the gravure roller surface onto the first web surface. Spaced apart clusters of spaced apart droplets of adhesive are transferred in this manner onto the first web surface corresponding only to those surface areas of the second surface of the web which are pressingly contacted by the raised contact surfaces of the pressure roller.

In an embodiment, the raised contact surface portions on the pressure roller can be arranged in a regular pattern of spaced apart columns and spaced apart rows of raised contact surfaces. Typically, the pressure roller will have a generally cylindrical configuration including a core longitudinal axis. In a preferred embodiment, the repeating pattern of raised contact surface portions is disposed on the surface of the pressure roller in an angled manner such that a given row of raised contact surfaces is helically offset with respect to the core longitudinal axis. This deployment of contact surfaces facilitates a smoother more accurate transfer of adhesive clusters with less vibration and chatter.

Droplets of adhesive may be provided in the depressions on the gravure roller surface by submerging a portion of the gravure roller surface in a reservoir of adhesive. Excess adhesive may be removed from the surface of the gravure roller from all but the depressions with a doctor blade. The adhesive reservoir and doctor blade are disposed at a position along the path of rotation of the gravure roller located before the nip point where the pressure roller contact surfaces make contact with the surface of the gravure roller.

In an alternate method, when using difficult to adhere films or relatively temperature sensitive nonwoven web materials, it may be preferable to deposit the adhesive droplets onto the film surface instead of the web surface.

This may be achieved by reversing the positions of the rolled film and rolled nonwoven web supplies.

In still another aspect, the present invention provides, in an embodiment, new and improved disposable surgical drapes and gowns comprising the new and improved laminate materials. The drapes comprise a piece of a disposable laminate in accordance with an embodiment of this invention and may include fenestrations and one or more panel elements secured to the laminate panel adjacent a fenestration or adjacent a peripheral edge of the laminate panel.

In an embodiment, new and improved surgical gowns are provided comprising a body portion and two sleeves connected to the body portion. The body portion includes a front panel and two opposed back side panels connected to the front panel. A tie member is attached to the body for securing the gown in a closed position on the wearer. The sleeves, the body portion or both comprise a disposable laminate in accordance with an embodiment of this invention. In a preferred embodiment, the body and sleeves are made from a breatheable impervious disposable laminate as described herein. Alternatively, single panel surgical gowns comprising a new and improved disposable laminate in accordance with this invention are also fully contemplated herein.

A major advantage provided by the new and improved laminates, drapes and gowns in accordance with embodiments of this invention is that these products exhibit improved softness, hand and improved drapability in comparison with commercially available drapes and gowns.

Another advantage provided by the new and improved laminates and gowns is that they exhibit improved conformability to application so that undesirable channeling of fluids under surgical gloves is substantially reduced or eliminated.

A further advantage provided by the laminates, drapes and gowns in accordance with the present invention is that they are characterized by improved aesthetic qualities having a pleasing appearance and texture.

Still another advantage provided by the laminates and finished articles in accordance with embodiments of this invention is that dramatic reductions in the amount of adhesive afford the possibility of increased chemical absorption. For example, higher percentages of unbonded portions of the nonwovens may realize their full power of absorbency.

Still a further advantage provided by the laminates and articles in accordance with embodiments of this invention is the possibility of increased mechanical absorption of fluids because the more open three dimensional configuration captures additional fluids.

Other advantages provided by the present invention will become apparent from the following Detailed Description and Illustrative Drawings, in which:

DETAILED DESCRIPTION OF THE PRESENTLY PREFERRED EMBODIMENTS

The present invention provides new and improved disposable surgical laminates and new and improved methods for making them. The present invention also provides new and improved disposable surgical drapes and surgical gowns made from the improved surgical laminate materials.

Figure 1:
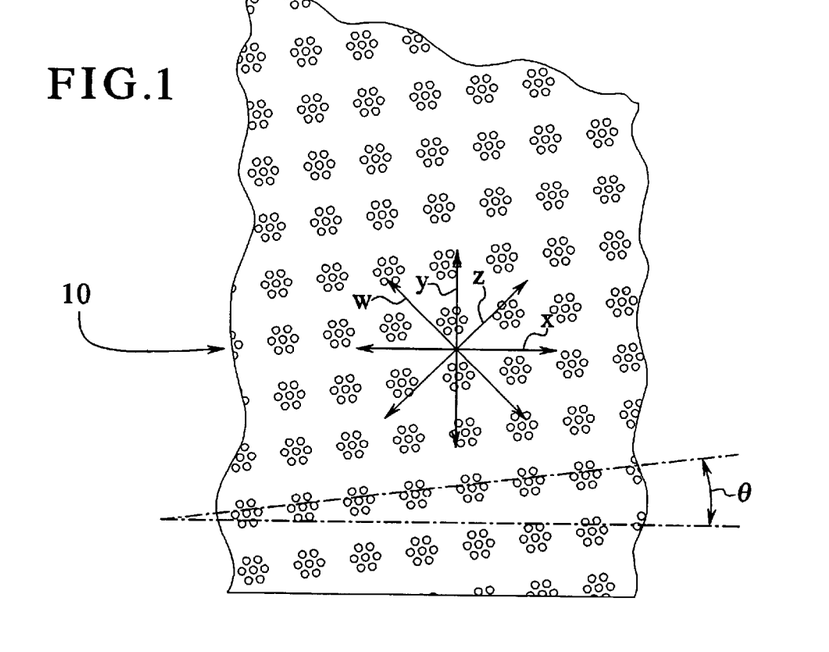
FIG. 1 is a top plan view of the new and improved disposable surgical laminate in accordance with an embodiment of the present invention.
Figure 2:
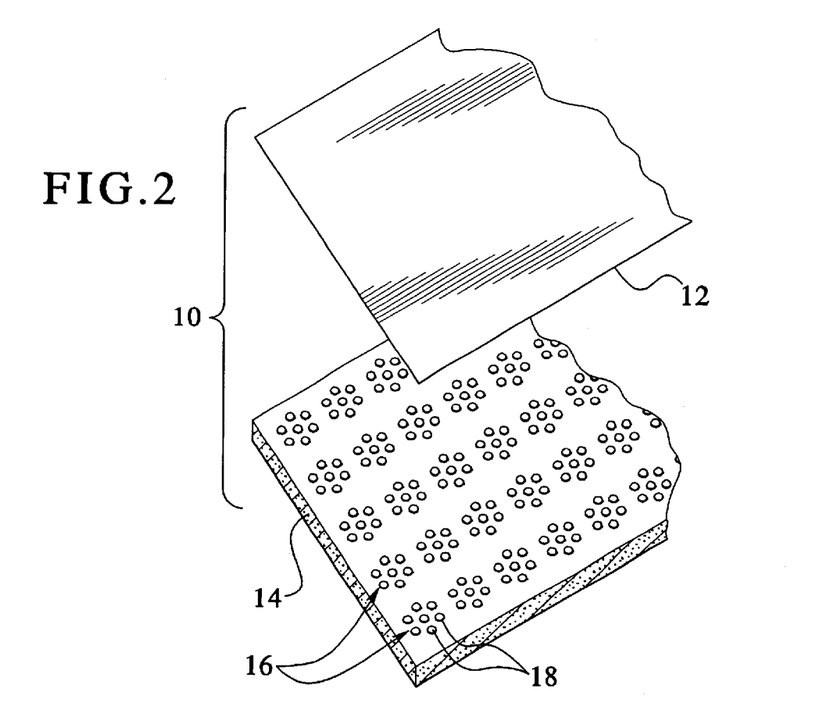
FIG. 2 is an exploded perspective view of the new and improved disposable surgical laminate shown in FIG. 1.
Figure 3:
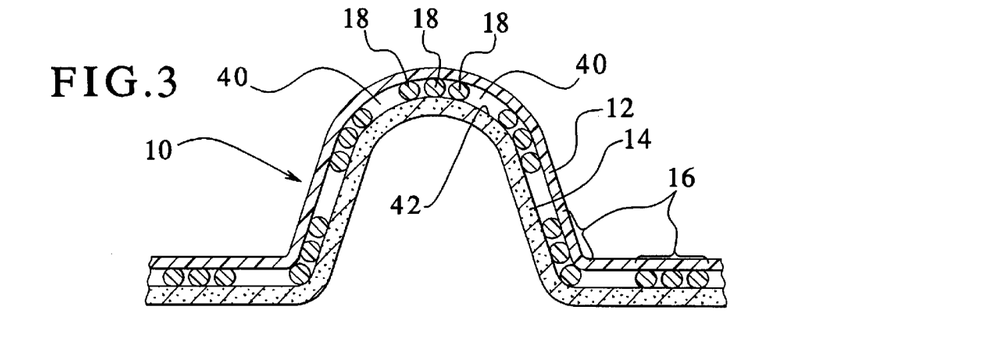
FIG. 3 is an elevated cross-sectional view of the new and improved disposable surgical laminate as shown in FIGS. 1–2 showing a fold in the laminate to illustrate the flexibility of the laminates in the bonding areas which contributes to improved softness and drapability.

More particularly, and referring now to FIG. 1, a section of a new and improved disposable surgical laminate generally indicated by reference numeral 10, is shown. As shown in FIGS. 1–3, disposable surgical laminate 10 comprises a film layer 12, a nonwoven web layer 14 and a plurality of unbounded adhesive clusters 16. Each unbounded adhesive cluster 16 comprises a perimeterless grouping of a plurality of discrete, individual spaced apart adhesive droplets 18 securing nonwoven web 14 and film layer 12 together. As depicted in the preferred embodiment shown in FIGS. 1–3, clusters 16 comprise spaced apart droplets 18 arranged in adjacent rows in a 2-3-2 pattern. Although, a 2-3-2 spacing pattern or configuration is shown in this embodiment other droplet patterns may be used.

Clusters 16 of spaced apart droplets 18 should generally be unbounded or perimeterless. By this is meant that there is no surrounding linear boundary of adhesive circumscribing the droplets 18 which may rigidify the laminate at the cluster bond site or prevent flexible folding to occur in any of the w, x, y or z directions as shown in FIG. 1. As is illustrated in FIG. 3, the spaced apart arrangement of droplets 18 permits folding or bending of laminate 10 in any of the w, x, y or z directions within a given cluster 16. The spaced apart array of clusters 16 permits folding of laminate 10 between spaced apart clusters 16, and the spaced apart configuration of droplets 18 permits folding of laminate 10 within or through the clusters 16, providing improved overall softness, hand and drapability for laminate 10. For example, if laminate 10 is draped over a table edge, a fold line is defined extending in the plane of the laminate material, such as fold axes w, x, y or z. Laminate 10 will bend, flex and fold along the table edge fold line in a compliant conforming manner bending within the clusters 16 located along the fold line and in the unbonded portions of laminate 10 located along the fold line between the clusters 16. The spacing between droplets 18 permits either the film layer 12 or the web layer 14 to bend, fold or compress even between the droplets 18 along a given fold line providing softer feel and better drapability.

Thermal bonding or ultrasonic welding of thermoplastic layers does not provide the same degree of softness, flexibility or drapability, because the bonding points are hard, stiff segments. The bonded segments are rigidly fused and not flexibly, bendably bonded together. Similarly, with earlier adhesive bonding methods, substantially the entire surfaces of the film layer and web layer were bonded together which resulted in a board-like stiffness for the laminates. Thermobonding or even adhesive bonding using hollow bonding shapes still provides stiff perimeter lines in the bond areas which inhibit foldability in the bonding site, thereby adversely impacting overall softness and drapability.

Figure 4:
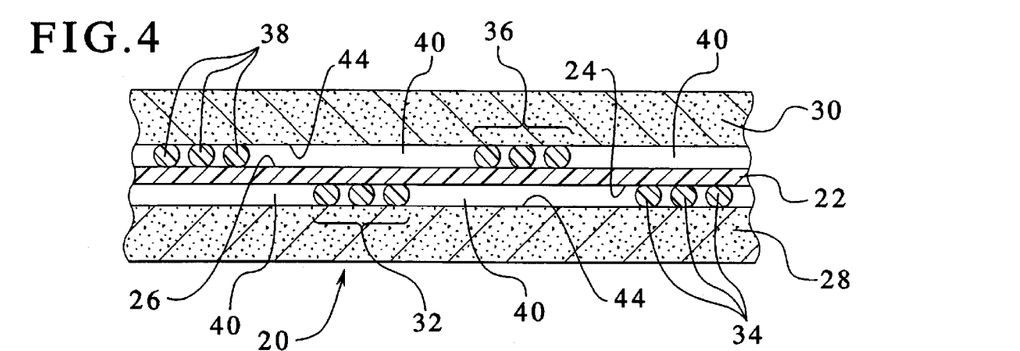
FIG. 4 is an elevated cross-sectional view of a new and improved three-ply or triplex disposable surgical laminate in accordance with a preferred embodiment of the invention.

In accordance with the preferred embodiment shown in FIGS. 1–3, two ply laminates 10 are shown. In FIG. 4, an alternate embodiment comprising a three-layer multi-ply, or triplex, laminate 20 is shown. Triplex laminate 20 comprises an intermediate film layer 22 having a first major surface 24 and an opposed second major surface 26. A first nonwoven web layer 28 is disposed adjacent first major surface 24 of film layer 22. A second nonwoven web layer 30 is disposed adjacent second major surface 26. A first plurality of spaced apart unbounded adhesive clusters 32, each comprising a plurality of discrete spaced apart droplets of adhesive 34 secures first nonwoven web 28 to first major surface 24 of film layer 22. A second plurality of spaced apart unbounded adhesive clusters 36, each comprising a plurality of discrete, spaced apart droplets of adhesive 38 secures second nonwoven web 30 to second major surface 26.

Although this is not a requirement for triplex laminates and is not shown in FIG. 4, in an embodiment, the first plurality of adhesive clusters 32 may be disposed in overlying registering alignment with the second plurality of adhesive clusters 36, such that droplets 34 are aligned with droplets 38. Although laminate 10 is a duplex laminate as shown and laminate 20 is a triplex laminate, additional nonwoven web layers or other layers may be added to laminate 10 or to laminate 20 using the same cluster bonding structure and methods, if desired.

The new and improved cluster bonded duplex laminates 10 and triplex laminates 20 have a three dimensional structure which not only provides improved softness and drapability, but also provides improved chemical and mechanical absorption by opening up large adhesive free intermediate areas in the laminate and exposing large amounts of internal web surface areas. The interlaminar spaces 40 represent internal volume which permits mechanical absorption of fluids by capillary action and wicking to occur. The exposed unbonded internal web surfaces such as surfaces 42 and 44 as shown in FIGS. 3 and 4, respectively, allow chemically absorbent web fibers and nonwoven web structures, if selected, to further chemically and/or mechanically absorb fluids.

New and improved duplex laminates 10 and triplex laminates 20 permit a dramatic reduction in the amount of adhesive used to provide improved softness and cloth-like characteristics with a significant savings in materials costs. More particularly, satisfactory cluster bonded disposable surgical laminates such as laminate 10 and laminate 20 have been prepared with an amount of adhesive which is from about 5% to about 70% of the amount of adhesive previously used in duplex or triplex laminates, preferably with an amount of adhesive which is from about 10 to about 30% of the amounts previously employed and especially preferably with an amount of from about 14 to 25% of the previous amounts used. Expressed differently, the new and improved laminates in accordance with a preferred embodiment may contain as little as from about 0.25 to about 5% by weight adhesive. Improved costs are achieved by these significant reductions in adhesive content. Improved properties are achieved by the reduction in adhesive content and also by the cluster bonding configuration of the adhesive that is present.

The new and improved disposable surgical laminates of this invention preferably employ a thermoplastic polymer film as the film layer 12 or 22. Generally, any film forming thermoplastic polymer may be used. It is preferred that the thermoplastic polymer film be capable of withstanding commercial sterilization procedures which may include heat sterilization, ethylene oxide or other chemical sterilization, or radiation sterilization, such as gamma sterilization. Especially preferably, the thermoplastic polymer film selected will be suitable for gamma sterilization.

Thermoplastic polymer films which may be used as film layer 12 or 22 herein include olefinic polymers and copolymers, polyester polymers and copolymers and polyamide polymers and copolymers, to name but a few. Olefinic polymers and copolymers may include polyethylenes; polypropylene; ethylene-propylene copolymers; copolymers of ethylene with other ethylenically unsaturated monomers such as vinyl halides, vinyl acetate, vinylidene halides, vinyl alcohol, styrene, (meth)acrylic acid, esters of (meth)acrylic acid and acrylonitrile, to name but a few; and rubbery copolymers such as ethylene-propylene rubber (EPR), ethylene propylene diene rubber (EPDM), styrene-acrylonitrile rubber (SAR), styrene-butadiene rubber (SBR), and acrylonitrile-butadiene elastomeric copolymers (BAN) to name but a few. The thermoplastic films may be cast films, extruded films or blown films. Vapor deposited or metallized polymer or metal films may also be used as the film layer. The films will generally have a film thickness of from about 0.25 to about 5.0 mils, preferably from about 0.4 to about 4 mils. Preferred films are those which are gamma sterilizable and for this reason polypropylene based films are less preferred. An especially preferred thermoplastic polymer film for use as film layer 12 or 22 is a blended polyethylene film comprising linear low density polyethylene (LLDPE) and low density polyethylene and having a film thickness of from about 0.5 to about 2.0 mil. Suitable thermoplastic films render the laminates fluid impervious and prevent fluid transfer between patient and surgical personnel across the film barrier layer.

In accordance with a preferred embodiment, the new and improved laminates are breatheable and impervious. In these embodiments, a breatheable impervious thermoplastic polymer film layer is used for film layer 12 or 22. The breatheable film layers may comprise monolithic films or microporous films which are known to those skilled in this art. Especially preferred monolithic films comprise HYTREL® thermoplastic polyether-ester block copolymer elastomer films available from E.I. duPont de Nemours and Company and ARNITEL® copolyester elastomer films comprising hard and soft segments of polybutylene terephthalate and amorphous polyesters or polyethers, respectively, available from DSM Engineering Plastics. Other breatheable impervious films such as polyetheramide films sold under the tradename PEBAX® from Elf Atochem may be used, as well as breatheable films comprising polyurethane which are commercially available from a number of sources.

The nonwoven webs for use as web layers 14, 28 and 30 as shown in FIGS. 1–4 may comprise generally any nonwoven web desired. Preferably, the nonwoven webs are selected from nonwoven web materials which are gamma sterilizable, and for this reason, polypropylene based nonwovens are less preferred. A major advantage of the new and improved cluster bonded laminates of this invention is that the nonwoven web materials are not required to be thermoplastic nonwovens but may also comprise natural fibers, regenerated fibers or synthetic fibers which are not thermoplastic in nature. For example, specialty laminates may include glass, metal or ceramic fiber containing nonwovens. A preferred class of nonwoven web layers does comprise thermoplastic polymer nonwoven web materials. Another preferred class of nonwoven web layers comprises rayon fibers, i.e. regenerated cellulose wood pulp fibers, for use in laminates where absorbency is a desired characteristic or property. The nonwoven web materials may be wet laid, dry laid, spunlaced and spunbonded-melt blown-spunbonded (SMS) types well known to those skilled in this art.

Preferred thermoplastic polymer nonwoven webs for use herein include 100% thermal bonded polyester staple fiber nonwovens available from Freudenberg, Durham, N.C. An adhesive bonded polyester fiber nonwoven may also be used which is commercially available from PGI, Mooresville, N.C. When absorbency is important, a rayon fiber nonwoven may be used. In a preferred embodiment, a biodegradable thermoplastic polymer web comprising spunlaced polyvinyl alcohol fiber nonwoven web is used. For non-gamma sterilized embodiments, an SMS polypropylene nonwoven web layer may be employed.

Especially preferred nonwovens for use as web layers 14, 28 or 30 include natural fiber/polyester fiber blend nonwovens such as spunlaced 55% cellulose wood pulp fiber/45% polyester nonwovens sold under the tradenames OPTIMA® and SONTARA®, available from E.I. du Pont de Nemours and Company. The proportions of different fibers in the blends may vary and the nonwovens still find application herein.

Another special class of thermoplastic polymer nonwovens for use in a preferred embodiment are nonwovens based on or comprising bicomponent or sheath/core fibers. These bicomponent fibers can comprise polyethylene/polyamide fibers, polyethylene/polyester fibers and polyester/polyester fibers, to name but a few. Spunbonded bicomponent fiber nonwovens of the type which may be used herein are commercially available from BBA, Simpsonville, S.C.

The adhesives for use herein for cluster bonding the film layer and nonwoven web layer(s) together may generally comprise thermoplastic polymer adhesives and thermoplastic hot melt adhesives are generally preferred. The hot melt adhesives may comprise ethylene vinyl acetate, styrene, polyolefins, modified polyolefins, polyamides and/or polyesters. A presently preferred hot melt adhesive for use herein comprises ethylene vinyl acetate (EVA) available from ATO Findley, Wauwatosa, Wis. Any suitable adhesive may be used, however, the adhesive is preferably thermoplastic and is able to withstand gamma irradiation sterilization.

In accordance with the present invention, new and improved laminate materials suitable for disposable surgical applications as well as for different non-surgical uses may be prepared from film layers and web layers having a broad range of basis weights and a broad range of layer thicknesses. In accordance with the preferred embodiments, new and improved disposable surgical laminates having improved softness and drapability will comprise film layers having a layer thickness of from about 0.4 to about 4.0 mil and having basis weights of from about 0.25 to about 5.0 ounces/square yard, preferably from about 0.3 to about 4.0 ounces/square yard. The nonwoven webs may have basis weights of from about 0.25 to about 7.0 ounces/square yard, preferably from about 0.3 to about 5.0 ounces/square yard. The amount of adhesive used may vary but preferably comprises from about 0.025 to about 0.250 ounces/square yard, especially preferably from about 0.040 to about 0.18 ounces/square yard. In a preferred embodiment, new and improved disposable surgical duplex laminates may generally comprise from about 30% to about 50% by weight thermoplastic polymer film, from about 40% to about 60% by weight nonwoven web and from about 0.5 to about 15% by weight of adhesive based on the weight of the overall laminate. Actual proportions may vary for these laminates and values for triplex laminates may vary, which is why it may be more helpful to identify suitable basis weights for the layers.

Figure 5:
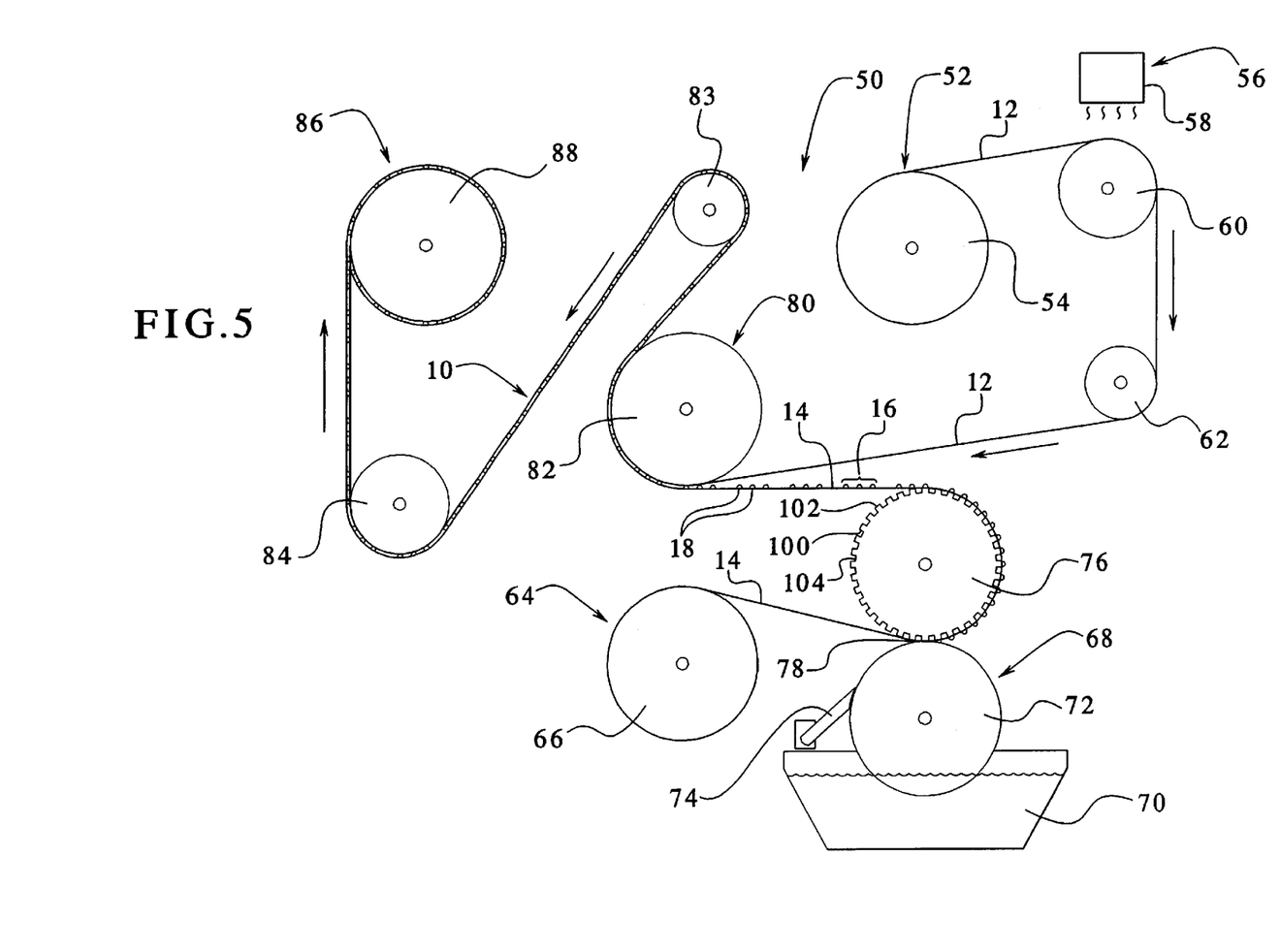
FIG. 5 is a schematic view of a laminating apparatus and method which may be used to form the new and improved disposable surgical laminates in accordance with another embodiment of the present invention.
Figure 6:
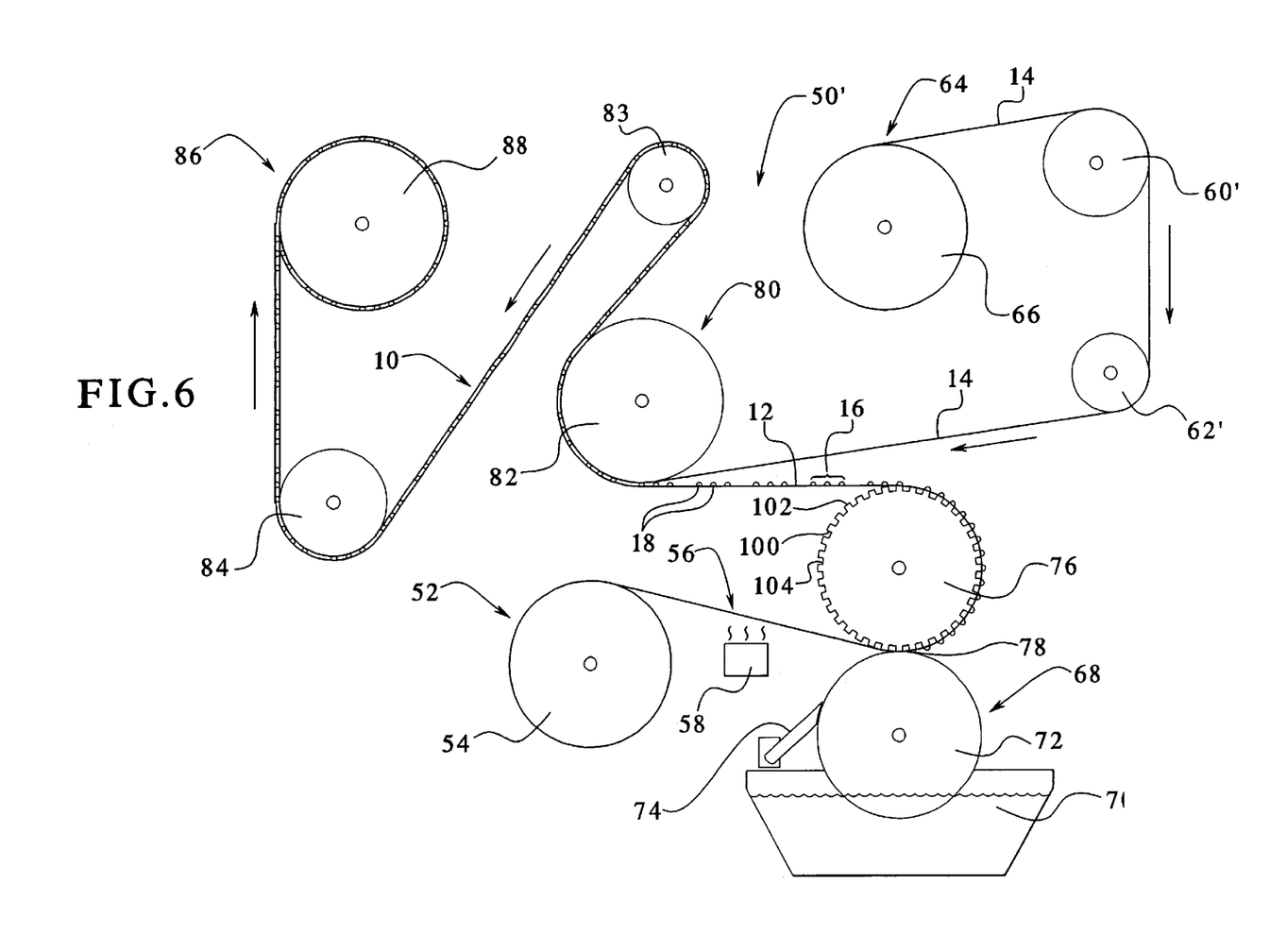
FIG. 6 is a schematic view of the laminating apparatus similar to FIG. 5 but showing the position of the film feed and web feed reversed to deposit droplets of adhesive on the film surface instead of on the web surface.
Figure 7:
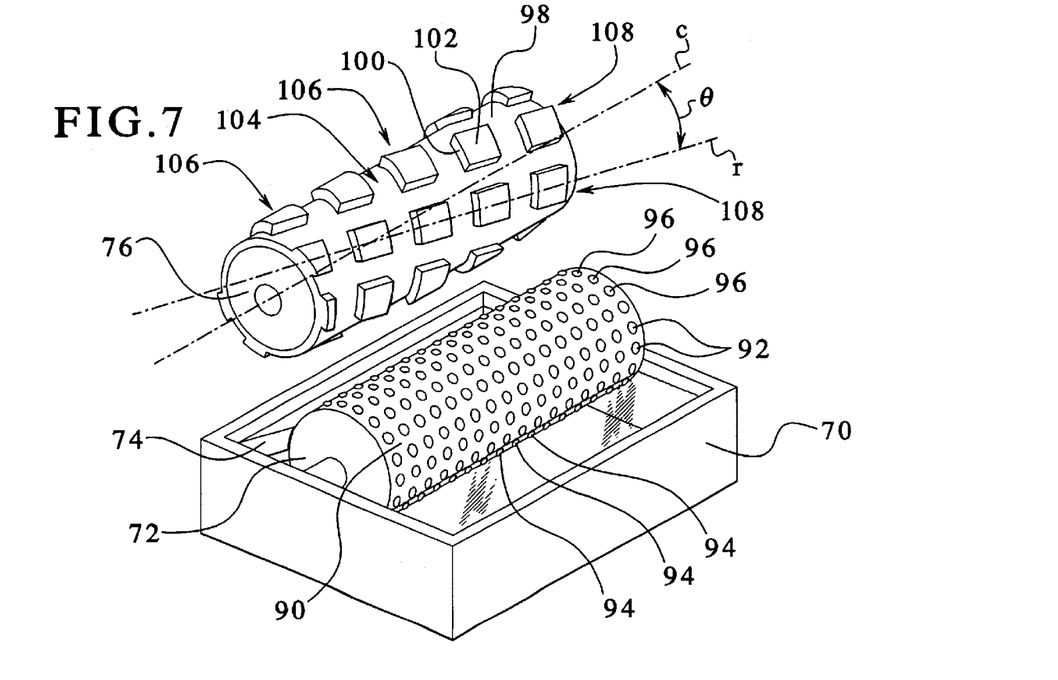
FIG. 7 is an enlarged perspective view of a portion of the apparatus of FIG. 5 illustrating the nip formed between an elastomer covered pressure roller having raised contact areas and a surface of a gravure roller having a plurality of adhesive droplet containing depressions.

In accordance with an alternate aspect of the invention, a new and improved method for making the new and improved disposable surgical laminates 10 or 20 is also provided. Referring now to FIGS. 5–7, a modified laminator apparatus 50 and method for making the new and improved disposable surgical laminates is illustrated. Laminating apparatus 50 includes a machine frame, not shown, upon which various rollers, drive mechanisms and other structures are mounted and positioned for operation. Laminating apparatus 50 in FIG. 5 is set up so that discrete spaced apart droplets of adhesive such as 18, 34 and 38 are deposited on a surface of a nonwoven web layer such as 14, 28 or 30 in a regular pattern of unbounded spaced apart clusters of adhesive droplets such as clusters 16, 32 and 36.

In accordance with the embodiment shown in FIG. 6, the laminating apparatus 50' is set up differently so that adhesive droplets are deposited in spaced apart clusters on a surface of the film layer instead of the web layer. The laminator set up in FIG. 6 is employed when preparing laminates having a film layer type which is difficult to bond and/or in those instances where the nonwoven web layer comprises a temperature sensitive material.

In most respects, the structure and operation of laminators 50 and 50' are substantially the same. Both of laminators 50 and 50' include a film supply station or section, generally indicated at 52, including a rolled film supply 54, a corona discharge treatment section 56 with a corona discharge apparatus 58 and in the FIG. 5 arrangement, guide rollers 60 and 62. A nonwoven web supply station or section 64 is provided including a rolled web supply 66 and in the FIG. 6 arrangement, guide rollers 60' and 62'. An adhesive transfer station or section 68 is provided including an adhesive reservoir or supply 70, an etched gravure roller 72 with a doctor blade 74 and an elastomer covered pressure roller 76 forming a nip 78 between gravure roller 72 and pressure roller 76. A laminating station or section 80 is provided including a chill roller 82 and a guide roller 83. A guide roller or rollers 84 may be employed to guide the assembled laminate to a laminate removal station or section 86 including a laminate take up roller 88. As is well known to those skilled in this art, appropriate drivers (not shown) are employed as desired to turn take-up roller 88, gravure roller 72 and pressure roller 76 to move the film 12 or 22, web 14, 28 or 30 and laminate materials 10 and 20 through laminating apparatus 50.

Laminators such as 50 and 50' are commercially available from a number of sources. A preferred laminator is available from Faustel Laminators, Milwaukee, Wis. Preferably, the laminator is adapted to run wide film and web widths of from about 20 to 120 inches in width and can run at from about 100 feet/minute to above about 1000 feet/minute. An especially preferred Faustel Laminator accepts 84 inches wide web and film starting materials and can operate commercially at rates of from about 100 feet/minute to above 800 feet/minute.

In accordance with the new and improved laminator apparatus and method, a special modification is made to provide a specially designed elastomer covered pressure roller 76 for use with the etched rotogravure roller 72 in the adhesive transfer station 68 so that the laminator 50 or 50' is properly modified to transfer clusters 16 of unbounded adhesive droplets 18 at the adhesive transfer station 68. More particularly and referring now to FIG. 7, the details of the adhesive transfer station 68 are shown in greater detail.

As shown in FIG. 7, etched gravure roller 72 has a circumferential surface 90 including a plurality of etched depressions 92 therein. Depressions 92 are disposed in a regular array of columns 94 and rows 96 of depressions 92. In a preferred embodiment, gravure roller 72 is provided with depressions etched to a depth of up to about 0.030 inch and providing about 110 depressions 92 per square inch. Other depression depths and spacings may be provided on gravure roller 72 as will be readily apparent to those skilled in this art.

Gravure roller 72 is mounted for rotational movement so that a portion of its surface 90 is submerged in a heated reservoir 70 of hot melt adhesive maintained at temperatures for example of from about 200–400° F. As gravure roller 72 is rotated clockwise through the adhesive bath as shown in FIG. 7, adhesive is picked up from the bath 70 and coats the surface 90 and fills the depressions 92. Upon further clockwise rotation, a doctor blade 74 contacts surface 90 and wipes substantially all of the adhesive from surface 90 except for the depressions 92. Excess adhesive removed by the doctor blade 74 is permitted to fall back into reservoir 70. The surface 90 of the gravure roller 72 carries small spaced apart droplets of adhesive in the depressions 92 and substantially no adhesive on remaining portions of gravure roller 72 as the surface portion of roller 72 is rotated from the point of contact of the doctor blade to the nip area 78.

The modified laminators 50 and 50' include a new and improved elastomer covered pressure roller 76 best illustrated in FIG. 7. As depicted therein, pressure roller 76 has a circumferential bearing surface 98 including a plurality of raised, upstanding, spaced apart island-like projections 100. Raised projections 100 have raised end wall contact surfaces 102. Raised projections 100 effectively configure the circumferential bearing surface 98 so that it has a plurality of relatively raised contact surfaces 102 separated by a plurality of grooves 104. In the preferred embodiment shown in FIG. 7, raised contact surfaces 102 have a generally four-sided square, configuration. Raised contact surfaces 102 could also have other configurations including rectangular, diamond-shaped, circular, triangular and oval-shaped as desired. Preferably, the elastomeric covering defining circumferential bearing surface 98, projections 100, raised contact surfaces 102 and grooves 104 is a molded strip of elastomer material such as silicone rubber, neoprene rubber, or any thermoplastic elastomer, e.g. SBR, EPR, EPDM, polyurethane elastomers or the like, which is secured onto a roller base by means of adhesive or other securement or bonding method.

In accordance with the preferred embodiment shown in FIG. 7, the island-like projections 100 and raised contact surfaces 102 are disposed in a regular array of columns 106 and rows 108 of projections. Pressure roller 76 has a generally cylindrical configuration including a longitudinally extending core axis, c, as shown. In accordance with the preferred embodiment depicted in FIG. 7, the elastomeric covering is applied to the pressure roller in an angled or offset manner as shown by row axis, r, and angular offset, θ, in FIG. 7. In accordance with this arrangement, a given row of contact surfaces 100 is helically offset with respect to the core longitudinal axis c. The helical offset or spiral disposition of each row 108 of contact surfaces 102 permits gradual sequential engagement of contact surfaces 102 with the surface 90 on gravure roller 72 from one end of each row 108 to the other, i.e. from left to right as shown in FIG. 7 as pressure roller 76 is rotated in a counterclockwise direction against the clockwise rotation of the gravure roller 72. This arrangement promotes a smooth adhesive transfer operation. By way of comparison, if the row axis r is made to extend generally parallel to core axis c, then during rotation of the pressure roller 76 against gravure roller 72, all of contact surfaces 102 in a given row 108 will make contact with gravure roller 72 at about the same time. Upon further rotation, a groove row is presented toward gravure roller 72, followed by a raised row of contact surfaces. Upon continuous rotation, this arrangement may cause chatter or bumping between raised contact surfaces 102 and surface 90 on gravure roller 72 which is undesirable from the standpoint of accuracy of adhesive transfer and may cause excessive wear to roller bearings in commercial operations. As shown in FIG. 1, a row of clusters is not deposited parallel to a width axis but instead is deposited at an angled orientation, θ, by virtue of this arrangement.

Referring again to FIGS. 5 and 6, the nonwoven web layer 14 or the film layer 12, respectively is fed from the respective supply rolls 66 or 54 into the nip 78 so that the raised contact surfaces 102 on pressure roller 76 press against the rear or backside surface of web 14 or film 12, pressing portions of the front side surface of web 14 or film 12 against portions of the circumferential surface 90 on gravure roller 72. Any adhesive droplets in the surface 90 which make pressing contact with web 14 or film 12 which are being urged against surface 90 by raised contact surfaces 102 are lifted off of surface 90 and onto the surface of web 14 or film 12. The droplets are transferred in discrete spaced apart droplet form and unbounded clusters of droplets corresponding to the shape of the contact surfaces 102 are transferred onto the front surface of web 14 or film 12.

In accordance with the preferred embodiments shown in FIGS. 5 and 6, the feed path of the web 14 or film 12 hugs the web or film against the contact surfaces 102 of the pressure roller 76 so that the web 14 or film 12 make tangential contact with the circumferential surface 90 of gravure roller 72 which maintains accuracy of droplet transfer. An important feature of laminators 50 and 50' is that adhesive does not contact pressure roller 76, so wicking of adhesive or adhesive build up on contact surfaces 102 or in grooves 104 does not occur, so that minimal, controlled amounts of adhesive are carefully transferred in controlled droplet cluster form.

As shown in FIGS. 5 and 6, the adhesive cluster carrying web 14 or film 12 travels from the adhesive transfer station 68 to the laminating station 80. In laminating station 80, the other film 12 or web 14 is superposed or aligned with and contacts adhesive carrying web 14 or film 12. The adhesive droplets make contact with the surface of the other film or web and the assembled laminate is maintained against a chill roller 82 maintained at temperatures of from about 30° F. to about 80° F. without limitation to cause the hot melt adhesive to cool and solidify to secure the web layer and film layer together. Thereafter, the cluster bonded laminate 10 or 20, passes around guide rollers 83 and 84 to be taken up on take up roller 88 in the laminate removal station 86. The accurate adhesive cluster transfer accomplished in laminators 50 and 50' provide anti-blocking characteristics in that adjacent folds of the laminate 10 or 20 taken up on take up roller 88 do not stick together which is a distinct advantage.

A major advantage provided by the new and improved laminator apparatus 50 and 50' and the new and improved laminating methods illustrated in FIGS. 5–7 is that cluster-bonded laminates 10 and 20 may now be prepared from a wide variety of film and web materials. The earlier requirement that the film layers and web layers be made from temperature matched thermoplastic materials is no longer necessary. Although, the present invention contemplates the manufacture of improved laminate constructions from a broad range of component materials, the invention makes possible a number of particular duplex and triplex cluster bonded laminate materials which are especially advantageous for use as disposable nonwoven surgical laminate materials and finished articles such as wipes, drapes and gowns.

One preferred disposable surgical nonwoven laminate embodiment comprises a duplex laminate including a film layer comprising an embossed blended polyethylene film and a nonwoven web layer comprising a spunlaced 55/45 cellulose wood pulp fiber/polyester nonwoven web cluster bonded to the film layer with an ethylene vinyl acetate adhesive. In an embodiment, a 1.25 mil embossed blended polyethylene film and a 1.82 ounce spunlaced Optima® nonwoven are used to form this preferred laminate.

Another preferred disposable surgical laminate in accordance with this invention comprises a duplex laminate comprising a 1 mil embossed blended polyethylene film layer and a 1 ounce adhesive bonded rayon staple fiber nonwoven web cluster bonded with EVA. This duplex is especially useful as an absorbent wipe, drape or gown panel. In the specified thicknesses recited above, cluster bonding provided a desired puckered or texturized surface characteristic for these laminates which provides improved mechanical wiping and absorption characteristics, without the need to use differential roller speed rates or other special adaptations previously employed to provide a textured surface wipe.

A further preferred disposable surgical laminate comprises a duplex laminate comprising a polyethylene film layer and a biodegradable polyvinyl alcohol nonwoven web layer.

Especially preferred duplex and triplex laminates are breatheable but impervious laminates especially suited for gowns including a monolithic thermoplastic elastomer film layer. Illustrative examples include an autoclavable but not gamma sterilizable duplex laminate comprising a HYTREL® polyester copolymer film layer and a 0.4 ounces/square yard SMS polypropylene nonwoven web layer cluster bonded with EVA.

Another duplex laminate suitable for use in drapes and gowns comprises a HYTREL® film layer and a 100% thermal bonded polyester staple fiber nonwoven web layer.

Another preferred duplex laminate comprises a thermoplastic film layer selected from a polyethylene film or a monolithic thermoplastic elastomer film and a spunbonded bicomponent fiber nonwoven web layer wherein the bicomponent fiber is selected from PE/nylon, PE/polyester and polyester/polyester bicomponent fibers.

Preferred triplex laminates for drapes and gowns may include double sided or mixed web types. A preferred triplex laminate comprises a 1 mil HYTREL® film layer cluster bonded to a 25 grams/square meter spunbonded PE/nylon bicomponent nonwoven web on a first side and cluster bonded to a 20 grams/square meter spunbonded PE/nylon bicomponent nonwoven web on the second side. Another preferred triplex laminate comprises a HYTREL® film layer, a PE/nylon bicomponent nonwoven web cluster bonded to a first side and a PE/polyester bicomponent nonwoven or a polyester/polyester bicomponent nonwoven web cluster bonded to the second film side.

A preferred absorbent triplex laminate for drapes comprises a blended polyethylene or HYTREL® film layer, a 100% thermal bonded polyester staple fiber nonwoven web cluster bonded to a first film surface and an adhesive bonded rayon staple fiber nonwoven cluster bonded to the second film surface.

Although the above mentioned duplex and triplex laminates have been specifically called out as especially preferred, modifications or changes may be readily made in accordance with this invention to provide further cluster bonded laminates having improved softness drapability and/or other desired characteristics.

Figure 8:
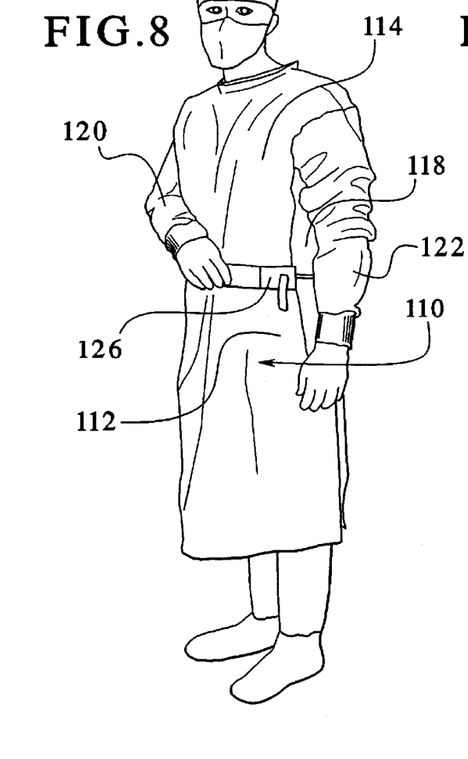
FIG. 8 is a perspective view of a surgeon wearing a new and improved disposable surgical gown in accordance with an embodiment of the invention.
Figure 9:
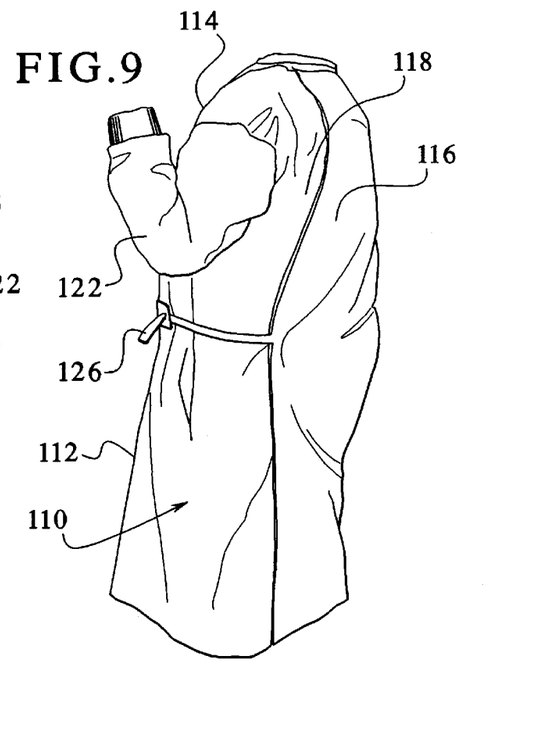
FIG. 9 is a perspective view of the surgical gown shown in FIG. 7 viewed from the back.
Figure 10:
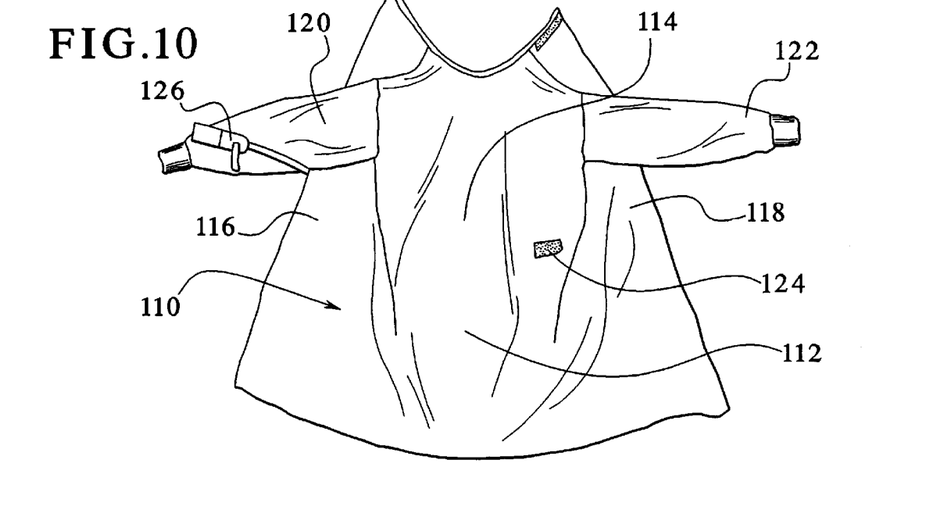
FIG. 10 is a perspective view of the surgical gown shown in FIG. 7 prior to donning.

Referring now to FIGS. 8–10, a typical medical or surgical gown 110 prepared with a new and improved disposable surgical nonwoven laminate in accordance with this invention is shown. Gown 110 comprises a body panel 112 including a front panel 114 and a pair of back panels 116, 118. Extending from each side of the body panel 112 are sleeves 120, 122. To wear the gown 110, the health care professional inserts a hand into each of sleeves 120, 122 with the front panel 114 of gown 110 facing outward. The gown 110 is extended onto the health care professional's arms and the back panels 116, 118 are wrapped around the rear portion of the health care professional in an overlapping fashion, as seen generally in FIG. 9.

In the preferred embodiment illustrated in FIGS. 8–10, the front panel 114 includes an area of adhesive 124 to which a tie 126 is secured. The adhesive 124 preferably comprises an area wider than the width of the tie 126 and of sufficient length to securely hold the tie 126. In the preferred embodiment described herein, the tacky area of adhesive 124 is preferably two inches in width and one inch in length.

In accordance with an embodiment of the present invention, new and improved disposable surgical gowns, such as gown 110, are provided by making front panel 114, back panels 116 and 118 and sleeves 120 and 122 out of a cluster bonded duplex laminate 10 or triplex laminate 20 in accordance with FIGS. 1–4. These laminates 10 and 20 are softer and more flexible. They have better hand and cloth like feel making them more acceptable to surgical personnel who must wear them. The improved softness and drapability characteristics permit the laminates to conform to the wrist without channeling, thereby reducing or eliminating the unwanted introduction of blood or body fluids under glove cuffs and into the surgeon's or nurse's gloves.

In accordance with a preferred embodiment, gown 110 comprises panels 114–118 and sleeves 120–122 prepared from the same duplex or triplex laminates which employs a breatheable impervious thermoplastic film layer of a monolithic copolymer film or a microporous copolymer film such as the above mentioned HYTREL® and ARNITEL® films. Breatheable impervious triplex laminates such as laminates 20 are especially preferred because a soft nonwoven layer is provided on the inside surfaces of the gown, for contact with the skin which is softer and more comfortable for the wearer.

Figures 11, 12, 13:
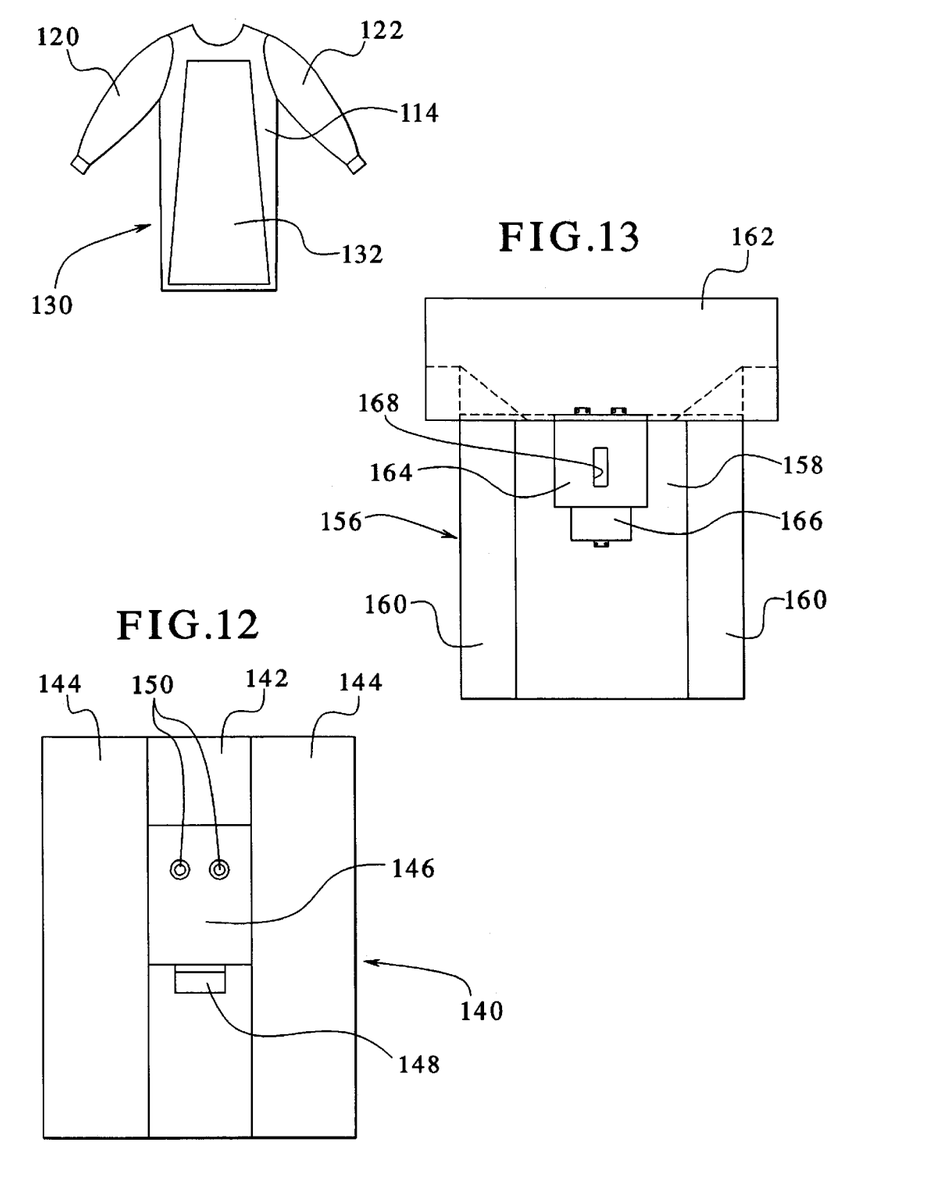
FIG. 11 is a front elevation view of another new and improved disposable surgical gown in accordance with an alternate embodiment.
FIG. 12 is a top plan view of a new and improved disposable angiography surgical shape in accordance with still another embodiment of the invention.
FIG. 13 is a top plan view of a new and improved disposable laparotomy surgical drape in accordance with a further embodiment of the invention.

In an alternate embodiment, such as gown 130 shown in FIG. 11, different panels and the sleeves may comprise different laminate materials or additional panels, treated panels or reinforcing panels may be added onto existing panels. More particularly, gown 130 is a surgical gown adapted for use in relatively high fluid volume surgeries, such as abdominal surgeries. In gown 130, front panel 114 and rear panels 116 and 118 are made from a first triplex laminate, such as 20. Sleeves 120 and 122 are made from a different absorbent triplex laminate including a breatheable impervious film layer, a soft polyester or bicomponent nonwoven web layer on an inner facing surface of the film layer and an absorbent rayon or thicker thermoplastic polymer nonwoven web on the outerfacing surface of the film layer. A separate absorbent panel 132 comprising a duplex laminate of a breatheable impervious film layer and an absorbent rayon or thermoplastic nonwoven web layer is sewn or adhesively bonded, web side out, onto the front panel 114 as shown. Other specialized panels, sleeves and gown structures will be readily apparent to those skilled in this art.

Referring now to FIGS. 12 and 13, new and improved disposable nonwoven surgical drapes in accordance with still another aspect of the invention are illustrated. FIG. 12 shows a preferred drape 140 for use in angiography procedures. Angiography drape 140 comprises a central cluster bonded triplex laminate sheet 142. A pair of lateral film sheets 144 are sewn or adhesively bonded to the long side edges of central sheet 142. Film sheets 144 are designed to hang over the sides of an operating table. A separate absorbent top sheet 146 such as a rayon nonwoven duplex laminate is sewn or adhesively bonded to central sheet 142. An instrument pad sheet 148 comprising a separate absorbent sheet is also sewn or adhesively secured to the bottom edge of absorbent top sheet 146. A pair of generally circular leg hole fenestrations 150 are provided extending through central sheet 142 and top sheet 146. In use, a patient's incision sites on a patient's legs are exposed through the fenestrations 150 so that drape 140 overlays the patient with the patient under the drape. The patient's legs are exposed through the fenestrations so that surgical cut downs may be made in the legs to perform angiography procedures. The instrument pad 148 is provided so that the surgeon has an identified place to put surgical instruments such as scalpels, clamps, silks or the like, adjacent the cut down site.

A new and improved laparotomy drape 156 is illustrated in the embodiment shown in FIG. 13. Laparotomy drape 156 also includes a central cluster bonded triplex laminate sheet and below the operating table lateral film sheets 160. A large rectangular cluster bonded duplex or triplex laminate panel is provided at the upper end to define an anesthesia screen drape sheet 162. The anesthesia screen drape sheet portion 162 overlays an upstanding screen or frame to isolate a patient's head from a surgical site in a well known manner. An absorbent top sheet 164 and instrument pad 166 are also provided as shown. Laparotomy drape 156 is provided with a rectangular fenestration 168 extending through absorbent top sheet 164 and central sheet 158 to expose an incision site on the patient. In accordance with this embodiment, the laparotomy drape 156 is placed over the patient and anesthesia screen. The panels of drape 156 may be sewn together or adhesively bonded together to provide the final drape assembly.

Drapes 140 and 156 are illustrative examples of drapes in accordance with this invention. Other materials and panels may be used in addition to or in place of any panels shown. Various surface treatments such as waterproofing or bacteriacides may be added onto any of the panels as desired.

The new and improved disposable surgical laminates and drapes and gowns prepared with them exhibit improved softness and drapability. Although cluster bonding may cause tensile properties to suffer slightly, tear strength properties of the subject cluster bonded laminates are generally improved. Moreover, the cluster bonded laminates exhibit unexpectedly improved absorbency characteristics for the same fibers and rayon containing puckered versions may improve absorbency even further.

Other objects and advantages of the present invention will become apparent from the following working examples.

EXAMPLE 1

In this example, a number of properties for a new and improved cluster bonded laminate in accordance with this invention were determined as well as for a commercially available extruded laminate. More particularly, the laminate of Example A was prepared in accordance with commercially methods comprising an extruded duplex laminate of a 1 mil embossed blended polyethylene film layer, and 100% rayon staple fiber nonwoven web layer was prepared. Another laminate was prepared in accordance with the present invention using cluster bonding methods. The laminate of Example 1 comprised a 0.75 mil embossed blended polyethylene film layer and a 1 oz. rayon nonwoven web layer cluster bonded with ethylene vinyl acetate adhesive droplets.

The laminate of Example A and laminate of Example 1 were tested for a variety of properties in accordance with standard testing methods including Elmendorf tear testing, grab tensile testing, Handle-O-Meter testing, dynamic absorbency testing, bond/peel strength testing, and fixed volume testing. Because of differences in these laminate materials, no direct comparisons may reasonably be made of physical properties based on mass or comfort criteria. These properties are reported here for information only as representative values for each of the respective laminate types. Nevertheless, surface absorption characteristics for these structurally different laminates may be meaningfully compared because this property is dependent on surface layer characteristics and generally is not dependent on different film thicknesses or the presence or absence of hot melt adhesive. The following standard test methods were used:

Thickness, in mils, was determined in accordance with ASTM D5729-97, wherein gauge of a material is placed under a constant load and thickness is measured;

Basis Weight, in ounces/square yard or grams/square meter, was determined in accordance with ASTM D3776-96;

Handle-O-Meter values, in grams, were determined in accordance with IST 90.3(95), INDA, Association of the Nonwovens Fabrics Industry Standard Test Method, wherein drapability of a fabric, film or laminate is indicated by its resistance to deflection when forced into a slot by a probe. Lower values indicate softer more drapable performance;

Elmendorf Tear, in grams, was determined in accordance with ASTM D5734-95 in which resistance of a notched structure to tearing with a free falling pendulum is determined;

Fixed Volume Absorbency, in seconds/milliliter, was determined in accordance with ASTM D824-94 (98), in which the time for the surface of a material to completely absorb 1 mL of water is determined;

Grab Tensile, in pounds, was determined in accordance with ASTM D5034-95, wherein the resistance of an intact structure to failure under a constant rate of applied pulling stress is measured;

Bond/Peel Strength, in ounces/inch of specimen, was determined in accordance with IST 110.3(95) wherein the resistance of various layers of a laminate to being separated is measured. Higher values indicate a more integral structure;

Dynamic Absorbency, in milliliters, was determined in accordance with EPA 300, an Allegiance Healthcare Corporation internal testing procedure which tests the ability of a fabric or a laminate to capture and retain fluids when such structure is placed on an inclined plane at a 12 degree angle. 100 milliliters of water are sprayed on the fabric and the amount of liquid retained and not run off is measured.;

Trapezoid Tear, in pounds, was determined in accordance with ASTM D5733-95, wherein a notch is placed in a specimen to propogate a tear and the resistance to tearing under a constant rate of stress is measured.

The averaged results obtained from testing five samples of each of these laminates are set forth in Table 1, as follows:

TABLE 1

Comparison Of Cluster Bonded vs. Extruded Nonwoven Laminates

| Example Laminate | A | 1 |
|---|---|---|
| PROPERTIES: | | |
| Thickness, in mils | 10.8 ± 0.5 | 14.7 ± 0.6 |
| Basis Weight, in ounces/sq. yd. | 2.30 ± 0.09 | 2.4 ± 0.1 |
| Handle-O-Meter, in grams | | |
| MD | 551 ± 48 | 643 ± 57 |
| CD | 165 ± 6 | 252 ± 15 |
| Elmendorf Tear, in grams | | |
| MD | 202 ± 21 | 234 ± 27 |
| CD | 320 ± 36 | 467 ± 54 |
| Fixed Volumes, in seconds/ml | 17.4 ± 2.6 | 15.1 ± 2.0 |
| Grab Strength (tensile) | | |
| PkL (lbs) | | |
| MD | 24.7 ± 0.7 | 24.4 ± 0.9 |
| CD | 10.3 ± 0.4 | 12.4 ± 0.7 |
| PkS (%) | | |
| MD | 14 ± 4 | 16 ± 4 |
| CD | 42 ± 3 | 49 ± 5 |
| Bond/Peel Strength, in oz./in. | | |
| kL | | |
| MD | 4.0 ± 2.0 | 20.2 ± 3.7 |
| CD | 2.5 ± 1.0 | 22.8 ± 4.3 |
| MD | 2.6 ± 1.3 | 9.1 ± 2.5 |
| CD | 1.5 ± 0.7 | DND* |
| Dynamic Absorbency, in grams | 11.4 ± 1.8 | 16.3 ± 1.7 |

*Did not de-laminate.

The results of Table 1, illustrate the excellent balance of physical properties obtained with the laminate of Example 1 in accordance with the present invention. More importantly, the results in Table 1 reveal a dramatic increase in absorbency for the laminate of Example 1 as compared to Example A, indicating that the cluster bonded laminates of Example 1 are especially useful for disposable surgical applications.

EXAMPLES 2–4

In the following examples, the physical properties of a new and improved cluster-bonded laminate in accordance with the present invention were compared with a conventional adhesively bonded laminate in non-sterilized, ethylene oxide (EtO) sterilized and gamma sterilized (100 kGy) forms. More particularly, in the following examples, a duplex laminate comprising a 1.25 mil embossed blended polyethylene film layer and a 1.82 ounce/square yard nonwoven web layer comprising 55%/45% of w/w spunlaced cellulose wood pulp fiber/polyester fiber nonwoven web was employed. In the control laminates of Examples B, C and D, the film layer and web layer were 100% surface bonded using an ethylene vinyl acetate adhesive applied on 100% of the web surface. In each of the laminates of Examples 2, 3 and 4 prepared in accordance with this invention, the film layer and web layer were cluster bonded together so that 25% of the web layer surface was provided with unbounded spaced apart adhesive droplets arranged in perimeterless spaced apart clusters. In Examples B and 2, the laminates did not undergo any sterilization processing prior to property measurement. In Examples C and 3, the laminates were subjected to two cycles of EtO sterilization in accordance with well known procedures prior to property testing. In Examples D and 4, the laminates were gamma sterilized by irradiation at levels of about 100 kGy in accordance with well known methods prior to testing.

The laminates of Examples B–D and 2–4 were tested in accordance with the procedures set forth in Example 1. In addition, the samples were also tested for trapezoid tear in accordance with standard methods described above.

The laminates tested by testing five samples and the averaged results obtained are set forth in Table 2 as follows:

TABLE 2

Comparison of Cluster Bonded vs. 100% Adhesively Bonded

| Laminate PROPERTIES | B | 2 | C | 3 | D | 4 |
|---|---|---|---|---|---|---|
| Thickness, in mils | 14.0 ± 0.5 | 15.4 ± 0.2 | 14.1 ± 0.4 | 15.4 ± 0.2 | 14.1 ± 0.4 | 15.5 ± 0.4 |
| Basis Weight, in oz/sq yd | 3.34 ± 0.11 | 3.01 ± 0.11 | 3.23 ± 0.04 | 3.02 ± 0.02 | 3.22 ± 0.05 | 3.01 ± 0.03 |
| Handle-O-Meter in grams | | | | | | |
| MD | 780 ± 89 | 585 ± 20 | 865 ± 12 | 599 ± 62 | 809 ± 39 | 570 ± 15 |
| CD | 548 ± 81 | 412 ± 35 | 524 ± 27 | 338 ± 52 | 546 ± 45 | 398 ± 26 |
| Grab Strength, MD | | | | | | |
| PkL in lbs. | 28.4 ± 2.7 | 23.0 ± 2.7 | 30.0 ± 3.2 | 23.6 ± 2.1 | 26.3 ± 1.3 | 21.3 ± 1.1 |
| PkS in % | 34 ± 5 | 37 ± 4 | 30 ± 7 | 38 ± 5 | 28 ± 3 | 36 ± 2 |
| Grab Strength, CD | | | | | | |
| PkL in lbs | 21.7 ± 1.5 | 18.0 ± 1.7 | 21.9 ± 2.5 | 17.4 ± 2.7 | 18.8 ± 2.0 | 17.0 ± 1.9 |
| PkS in % | 58 ± 6 | 52 ± 5 | 59 ± 3 | 50 ± 6 | 53 ± 4 | 55 ± 8 |
| Bond Strength, MD | | | | | | |
| Pkl in oz./in. | 29.9 ± 12.8 | 18.1 ± 2.0 | 34.5 ± 10.6 | 21.2 ± 1.8 | DND | DND |
| Avl in oz./in. | 22.0 ± 11.7 | 7.1 ± 3.7 | 24.4 ± 6.7 | 12.2 ± 1.3 | DND | DND |
| Bond Strength, CD | | | | | | |
| PkL in oz./in. | DND* | 20.9 ± 2.5 | 30.6 ± 2.7 | 23.6 ± 1.6 | DND | DND |
| AvL in oz./in. | DND* | 14.5 ± 3.0 | 27.2 ± 3.1 | 18.1 ± 1.9 | DND | DND |
| Trapezoid Tear, MD | | | | | | |
| PkL in lbs. | 6.7 ± 1.1 | 5.8 ± 1.2 | 6.1 ± 1.0 | 6.3 ± 0.8 | 4.9 ± 0.9 | 6.2 ± 1.3 |
| AvL in lbs. | 4.5 ± 0.5 | 3.6 ± 0.5 | 4.1 ± 0.5 | 4.0 ± 0.4 | 3.3 ± 0.6 | 3.9 ± 0.5 |
| Trapezoid Tear, CD | | | | | | |
| PkL in lbs. | 9.6 ± 1.6 | 9.5 ± 0.8 | 9.4 ± 0.4 | 8.4 ± 1.3 | 7.4 ± 0.8 | 6.7 ± 0.8 |
| AvL in lbs. | 6.6 ± 0.8 | 6.0 ± 0.5 | 6.2 ± 0.4 | 5.1 ± 0.5 | 5.0 ± 0.4 | 4.5 ± 0.4 |

As shown by the data of Table 2, the cluster bonded laminates of this invention of Examples 2, 3 and 4 exhibited significantly reduced Handle-O-Meter values corresponding to better softness as compared to the 100% surface bonded laminates of control Examples B, C and D. Although the grab strength and bond strength are somewhat lower for Examples 2, 3 and 4, this would be expected from the bonding geometries and lower proportion of adhesive. Although these values are slightly lower, the values obtained are still well within desired functional ranges. The trapezoid tear strengths were comparable. For surgical laminates for use in gowns, softness is extremely important to surgical personnel for their subjective comfort and to reduce or eliminate channeling as described above. The laminates of Examples 2, 3 and 4 clearly exhibited unexpectedly improved softness as compared to the commercial product of control Examples B, C and D.

Although the present invention has been described with reference to a number of preferred embodiments, other variations and permutations have been described herein or are known to those skilled in this art and are contemplated and included in this invention. Changes and modifications may be made in the embodiments described herein without departing from the invention. For example, although ethylene vinyl acetate is exemplified as the adhesive, any of the other adhesives described herein or known to those skilled in this art may be substituted. Other films and nonwoven webs may also be cluster bonded to provide advantageous laminates suitable for surgical or other uses. The new and improved cluster bonded laminates may be assembled with a variety of other films, fabrics or panel types to make improved drapes and gowns including without limitation, Kraton™ layers, Ultrasorb™ layers, IsoBac™ layers, Delnet™ layers, Optisorb™ layers, SMS layers, Dexter™ layers and unreinforced or reinforced Optima™ layers. Although, duplex or triplex laminates are illustrated, a pre-formed duplex or triplex laminate may have additional film or nonwoven web layers added thereto and affixed by cluster bonding methods as taught herein. All such obvious modifications may be made herein by those skilled in this art, without departing from the scope and spirit of the present invention as defined by the appended claims.

We claim:

1. A disposable surgical laminate comprising:
   a film layer;
   at least one nonwoven web layer; and
   a plurality of spaced apart unbounded adhesive clusters, each adhesive cluster comprising a plurality of discrete spaced apart droplets of adhesive securing the film layer and the web layer together.

2. A disposable laminate as defined in claim 1, wherein said film layer comprises a thermoplastic polymer film layer.

3. A disposable laminate as defined in claim 1, wherein said nonwoven web layer comprises a thermoplastic polymer nonwoven web.

4. A disposable laminate as defined in claim 1, wherein said adhesive comprises a thermoplastic polymer adhesive.

5. A disposable laminate as defined in claim 1, wherein the film layer comprises a polyethylene film and the nonwoven web comprises 55/45 w/w spunlaced nonwoven of cellulose wood pulp fibers/polyester staple fibers.

6. A disposable laminate as defined in claim 1, wherein the film layer comprises an embossed blended polyethylene film and the nonwoven web comprises an adhesive bonded rayon staple fiber nonwoven web.

7. A disposable laminate as defined in claim 1, wherein the film layer comprises a polyethylene film and the nonwoven web comprises a spunlaced polyvinyl alcohol fiber nonwoven web.

8. A disposable laminate as defined in claim 1, wherein the film layer comprises a breatheable impervious thermoplastic polymer film selected from the group consisting of monolithic thermoplastic polymer films and microporous thermoplastic polymer films.

9. A disposable laminate as defined in claim 1, wherein the film layer comprises a polyester copolymer thermoplastic elastomer film and the nonwoven web layer comprises a thermal bonded polyester staple fiber nonwoven web.

10. A disposable laminate as defined in claim 1, wherein the film layer comprises a polyester copolymer thermoplastic elastomer film and the nonwoven web layer comprises a bi-component fiber spunbonded nonwoven web.

11. A disposable laminate as defined in claim 1, wherein the film layer comprises a polyester copolymer thermoplastic elastomer film and the nonwoven web layer comprises a spunbonded-melt blown-spunbonded nonwoven web.

12. A disposable laminate as defined in claim 1, wherein the nonwoven web comprises a spunbonded bi-component fiber web wherein the bi-component fiber is a polyethylene over nylon sheath/core fiber.

13. A disposable laminate as defined in claim 1, wherein the nonwoven web comprises a spunbonded bi-component fiber web wherein the bi-component fiber is a polyethylene over polyester sheath/core fiber.

14. A disposable laminate as defined in claim 1, wherein the nonwoven web comprises a spunbonded bi-component fiber web wherein the bi-component fiber is a polyester over polyester sheath/core fiber.

15. A disposable laminate as defined in claim 1, wherein the adhesive droplets comprise a thermoplastic polymer based hot melt adhesive selected from the group consisting of ethylene vinyl acetate adhesives, polystyrene adhesives, polyolefin adhesives, polyamide adhesives, polyester adhesives and mixtures of two or more of any of the foregoing adhesives.

16. A disposable surgical laminate comprising:
  a thermoplastic copolyester elastomer film layer having first and second opposed major surfaces;
  a first nonwoven web layer disposed adjacent the first major surface;
  a second nonwoven web layer disposed adjacent the second major surface;
  a plurality of spaced apart unbounded adhesive clusters, each adhesive cluster comprising a plurality of discrete spaced apart droplets of adhesive securing the first web layer to the first major surface and securing the second web layer to the second major surface.

17. A disposable laminate as defined in claim 16, wherein the first and the second web layers comprise the same nonwoven material.

18. A disposable laminate as defined in claim 16, wherein the first and the second web layers comprise different nonwoven materials.

19. A disposable laminate as defined in claim 16, wherein the film layer comprises a monolithic copolyester elastomer film layer, the first web comprises a spunbonded bi-component polyethylene/nylon fiber nonwoven having a first basis weight and the second web comprises a spunbonded bi-component polyethylene/nylon fiber nonwoven having a second basis weight different from the first basis weight.

20. A disposable laminate as defined in claim 16, wherein said film layer comprises a thermoplastic copolyester elastomer film, the first nonwoven web comprises an adhesive bonded rayon staple fiber nonwoven and the second nonwoven web comprises a 100% thermal bonded polyester staple fiber nonwoven.

21. A disposable surgical drape comprising:
  a panel of a disposable laminate comprising a film layer; at least one nonwoven web layer; and a plurality of unbounded spaced apart clusters, each cluster comprising a plurality of discrete, spaced apart droplets of adhesive securing the film layer and the web layer together.

22. A disposable surgical gown comprising:
  a body portion and two sleeves connected to the body portion, the body portion including a front panel and two opposed back side panels connected to the front panel; and a tie member attached to the body for securing the gown in a closed position on a wearer, wherein the sleeves, the body portion or both, comprise a disposable laminate comprising: a film layer; at least one nonwoven web layer; and a plurality of unbounded spaced apart clusters, each cluster comprising a plurality of discrete, spaced apart droplets of adhesive securing the film layer and the web layer together.

* * * * *